US006743960B2

(12) United States Patent
Wang et al.

(10) Patent No.: US 6,743,960 B2
(45) Date of Patent: Jun. 1, 2004

(54) METHOD FOR OLIGOMERIZING OLEFINS TO FORM HIGHER OLEFINS USING SULFUR-CONTAINING AND SULFUR-TOLERANT CATALYSTS

(75) Inventors: Kun Wang, Bridgewater, NJ (US); Edward Ira Stiefel, Bridgewater, NJ (US); Abhimanyu Onkar Patil, Westfield, NJ (US); Stephen Zushma, Clinton, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 31 days.

(21) Appl. No.: 10/021,976

(22) Filed: Nov. 30, 2001

(65) Prior Publication Data

US 2003/0105374 A1 Jun. 5, 2003

(51) Int. Cl.$^7$ .............................. C07C 2/32; C07C 2/34
(52) U.S. Cl. .................. 585/512; 585/511; 585/512; 585/513; 585/515; 585/521; 585/522; 585/523; 585/526
(58) Field of Search .................. 585/511, 512, 585/513, 515, 521, 524, 525, 526

(56) References Cited

U.S. PATENT DOCUMENTS 4,533,651 A * 8/1985 Masters et al. ............. 502/117
6,120,692 A * 9/2000 Wang et al. ................ 210/749

OTHER PUBLICATIONS

The English abstract of Japanese patent 70007522B.*

Riccardo et al: Polymerization fo Styrene with Nikel Complex/Methylaluminoxane Catalytic Systems: Dec. 1997.*

* cited by examiner

Primary Examiner—Thuan Dinh Dang
(74) Attorney, Agent, or Firm—Joseph C. Wang

(57) ABSTRACT

The present invention is related to a method for oligomerizing olefinic monomers under oligomerization conditions to form higher olefins. The novel method comprises contacting a feed comprising the olefinic monomers with a catalyst composition comprising the reaction product of: (a) a compound having a formula selected from the group consisting of $M[S_2C_2(R^a R^b)]_2$ and $M[S_2C_6(R^1 R^2 R^3 R^4)]_2$, wherein M is a late transition metal, $R^a$, $R^b$, $R^1$, $R^2$, $R^3$ and $R^4$ are independently selected and may be the same or different and are selected from hydrogen, electron-withdrawing groups and unsubstituted and substituted hydrocarbyl groups; and (b) an activating cocatalyst. The improved method advantageously relates to oligomerizing olefinic monomers from feed streams having contaminants, especially sulfur-containing contaminants.

14 Claims, No Drawings

METHOD FOR OLIGOMERIZING OLEFINS TO FORM HIGHER OLEFINS USING SULFUR-CONTAINING AND SULFUR-TOLERANT CATALYSTS

BACKGROUND OF THE INVENTION

1. Field of the Invention

The present invention relates to oligomerization of olefins to form higher olefins, especially higher α-olefins. The instant invention also relates to the use of sulfur-containing and sulfur-tolerant catalysts to perform the oligomerization.

2. Description of the Related Art

Linear α-olefins are very important and versatile intermediates and building blocks for the chemical industry. The main applications for linear α-olefins are using $C_4$–$C_8$ α-olefins as co-monomers for polyethylene, $C_6$–$C_{10}$ α-olefins as feedstocks for plasticizers, and $C_{12}$–$C_{20}$ α-olefins for surfactants. Hydrocarboxylation of the $C_6$–$C_8$ α-olefins with cobalt carbonyl/pyridine catalysts gives predominantly linear carboxylic acids. The acids and their esters are used as additives for lubricants. The $C_6$–$C_{10}$ α-olefins are hydroformylated to odd-numbered linear primary alcohols, which are converted to phthalate esters (by reaction with phthalic anhydride) as polyvinyl chloride (PVC) plasticizers. Oligomerization of 1-decene, using $BF_3$ catalysts, gives oligomers used as synthetic lubricants known as poly-α-olefins (PAO) or synthetic hydrocarbons. The $C_{10}$–$C_{12}$ α-olefins can be epoxidized by peracids; this opens up a route to bifunctional derivatives or ethoxylates as nonionic surfactants.

Oligomerization of olefins is a major route that is currently used to make higher olefins, especially α-olefins. Other routes to α-olefins in decreasing importance are: paraffin wax cracking, paraffin dehydrogenation, and alcohol dehydration. A variety of catalysts for olefin oligomerization based on both early and late transition metals have been reported. One method uses Al-alkyls and is based on improvements to the original 1952 Ziegler's *Alfen process*. Another example is the Shell Higher Olefin Process (SHOP), in which a nickel hydride catalyst is used. While these catalysts are highly active and effective, they normally only work with clean feeds. In other words, possible contaminants such as $H_2$, CO, and especially mercaptans and thiophene, which are likely to exist in the feed, will poison the catalysts. Late transition metal catalysts are generally thought to be relatively insensitive to non.-sulfur-containing contaminants such as $H_2$ and CO; however, sulfur-containing contaminants are potent poisons to late transition metal catalysts. Removing the contaminants and cleaning up the feed adds cost to current olefin oligomerization processes. It is therefore desirable to develop a catalyst that can work directly with crude feed, thereby offering potential cost-saving advantages to the process of olefin oligomerization.

Research in the area of olefin oligomerization has been very extensive, and there is continuing interest in developing new and more robust catalysts. Catalysts ranging from transition metal complexes, organoaluminum compounds, and Lewis and Brønsted type compounds to inorganic salts and oxides have been reported.

Compared to the large body of literature available on olefin oligomerization catalysts with nitrogen and/or phosphorous ligands, there have been very few reports in the open literature describing olefin oligomerization catalysts with sulfur ligands. Masters, et al. (*J. Chem. Soc. Dalton Trans.* 1993, 59–68; U.S. Pat. No. 4,533,651; WO 83/02907) reported a system that comprises a nickel(II) complex and a co-catalyst. The nickel(II) complex is a square-planar species with a phosphine or phosphite ligand, a halogen ligand, and a substituted dithio-β-diketone ligand. The co-catalyst is an aluminum alkyl or an alkyl-aluminum chloride. The system catalyzes the oligomerization and/or isomerization of olefins. However, whether the system was contaminant-tolerant was not raised or discussed.

Japanese Patent No. 70007522 discloses a catalyst for co-oligomerization of butadiene and ethylene, wherein the catalyst consists of: (1) a metal complex having the formula $M(S_2C_2Ph_2)_2$, where M is Ni or Co and Ph is a phenyl radical; and (2) an organic Al compound of general formula $R_3Al$ or $R_2AlX$, wherein R is a hydrocarbon radical and X is a halogen atom. A mixture of isomers, including C6–C8 dienes, C10 trienes, and vinylcyclohexane, is formed as a result of coupling between butadiene and ethylene, and the product ratio is dependent on the metal used. No oligomerization product from ethylene was observed even though ethylene of pressures up to 700 psig was used.

Riccardo Po, et al., Journal of Polymer Science: Part A: Polymer Chemistry, Vol. 36, 2119–2126 (1998), discloses the polymerization of styrene using catalytic systems based on nickel derivatives and methylaluminoxane. Even though compound $Ni(Ph_2C_2S_2)_2$ (labeled PS8b) was listed among the catalysts tested, it did not produce any polymeric product, indicating that the compound was inactive in polymerizing styrene.

Organometallic catalyst technology is also a viable tool in oligomerization processes that produce linear α-olefins for use as feedstock in various other processes. However, one problem often encountered when using many of these catalyst systems is the propensity to produce α-olefins with very low selectivity (i.e., a Schulz-Flory type distribution with high k values). For instance, many of the linear α-olefins made today utilize a neutral nickel (II) catalyst having a planar geometry and containing bidentate monoanionic ligands. While these planar nickel (II) catalysts do produce linear α-olefins, these catalysis systems exhibit a Schulz-Flory type of distribution over a very wide range (i.e., $C_4$–$C_{30+}$).

To address the Schulz-Flory distribution problem, chromium metal-based catalysts have become popular for use in certain oligomerization processes. More precisely, chromium complexes have been used to oligomerize ethylene in order to form linear α-olefins with improved distributions. In fact, there have been reports of specific chromium catalysts that selectively trimerize ethylene to 1-hexene. See U.S. Pat. Nos. 5,814,575, 5,763,723 and 5,550,305. These techniques employ the use of a chromium compound in conjunction with aluminoxane along with one of a variety of compounds such as nitrites, amines and ethers. Unfortunately, while these techniques have been able to selectively produce α-olefins, polymer is formed as a co-product. Of course, when polymer is co-produced, the yield of desirable α-olefin products decreases accordingly. Also, as a practical matter, polymer build-up in the reaction vessel can severely hamper production efficiency, thereby limiting the commercial use of such processes.

As discussed above, the organometallic catalyst technology now being used to produce α-olefins has two major disadvantages. First, many of the organometallic catalysts produce α-olefins with a Schulz-Flory type distribution. Unfortunately this Schulz-Flory type distribution is not ideal when short chain α-olefins are desired; in other words, the selectivity is not good enough to maintain efficient processes. Because α-olefins are used as intermediates for specific products, α-olefins with certain chain lengths are desired. For instance, the following are examples of α-olefin chain lengths that would be desirable as feeds for certain product types: $C_4$ to $C_8$ for co-monomer in ethylene polymerization; $C_{10}$ for lube quality poly-α-olefins; and $C_{12}$ to $C_{20}$ for surfactant products. Thus, considerable inefficiency and waste are present when significant amounts of α-olefins are produced having chain lengths outside of the range required for production of a particular chemical. Second, while some of the current organo-metallic catalysts may improve selectivity, most also produce polymer co-products. This lowers the yield of the desired product. Additionally, the polymer co-products can also accumulate in the reaction vessel. These disadvantages make commercial use of organo-metallic catalysts less attractive and inefficient. Hence, there is still a need for improving the selectively and efficiency of linear α-olefin production.

SUMMARY OF THE INVENTION

The instant invention provides a method for selectively and efficiently producing higher olefins. The method includes contacting a feed comprising olefinic monomers under oligomerization conditions with a catalyst composition comprising a compound having the formula $M[S_2C_2(R^aR^b)]_2$ or $M[S_2C_6(R^1R^2R^3R^4)]_2$, wherein M is a late transition metal, $R^a$, $R^b$, $R^1$, $R^2$, $R^3$ and $R^4$ are independently selected and may be the same or different and are selected from hydrogen, electron withdrawing groups and unsubstituted and substituted hydrocarbyl groups; and an activating cocatalyst.

These and other features, aspects and advantages of the present invention will become better understood with regard to the following description and appended claims.

DETAILED DESCRIPTION OF THE INVENTION

Generally speaking, the method of the invention selectively produces oligomers. The term "oligomers" as used in this specification should be appreciated by one skilled in the art as meaning α-olefins having approximately three to forty carbon atoms. More preferred "short chain" linear α-olefins have approximately three to twenty carbon atoms. Most preferred short chain linear α-olefins have approximately four to twelve carbon atoms. The monomers used to produce the α-olefins are olefinic monomers such as ethylene, propylene and butenes. Higher olefinic monomers, such as hexenes and octenes, may also be employed to produce the α-olefins.

The invention provides a novel oligomerization method which utilizes a catalyst composition comprising a compound having the formula $M[S_2C_2(R^aR^b)]_2$ or $M[S_2C_6(R^1R^2R^3R^4)]_2$, wherein M is a late transition metal, $R^a$, $R^b$, $R^1$, $R^2$, $R^3$ and $R^4$ are independently selected and may be the same or different and are selected from hydrogen, electron withdrawing groups and unsubstituted and substituted hydrocarbyl groups; and an activating cocatalyst. Such compounds having formulas (I) $M[S_2C_2(R^aR^b)]_2$ and (II) $M[S_2C_6(R^1R^2R^3R^4)]_2$ are known in the art as metal dithiolene compounds. Dithiolene is a commonly used name for 1,2-enedithiolate or benzene-1,2-dithiolate and related dithiolates.

Compounds of formula (I) and (II) may be obtained by reacting a suitable source of metal with a suitable source of ligand, which may be obtained from commercial sources or prepared as described according to methods known in the art. The source of metal can also be obtained commercially. Typical examples of how to make the dithiolene compounds of formula (I) can be found in the literature, as disclosed in Schrauzer, et al., J.A.C.S., Vol. 87 (7), 1483–9 (1965), incorporated by reference herein. Anions of compounds of formula (II) can be made by reacting a metal salt with arene-1,2-dithiols and their analogs, as taught in Gray, et al., J.A.C.S., Vol. 88 (21), 4870–5 (1966), incorporated by reference herein. The neutral form of formula (II) is accessible by oxidation, either chemically or electrochemically. Additionally, compounds of formula (I) may be produced by the processes taught in U.S. Pat. No. 6,120,692 to Wang, et al., and Davison, et al., Inorganic Syntheses, Vol. 10, 8–26 (1967), both incorporated by reference herein.

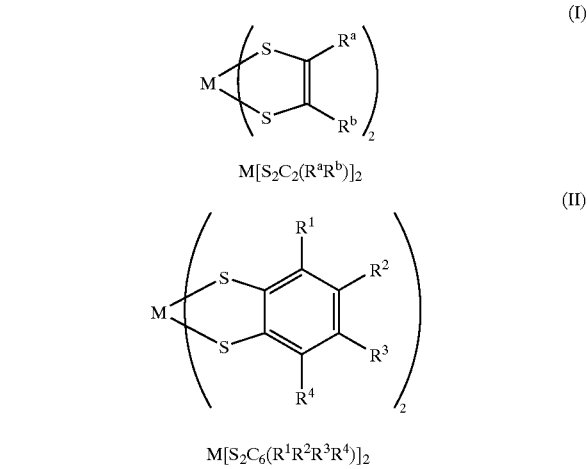

$M[S_2C_2(R^aR^b)]_2$ (I)

$M[S_2C_6(R^1R^2R^3R^4)]_2$ (II)

The structural formula for the transition metal bis (dithiolene) compounds are shown above in Formula (I) for $M[S_2C_2(R^aR^b)]_2$ and in Formula (II) for $M[S_2C_6(R^1R^2R^3R^4)]_2$.

In formula (I), M is a late transition metal, preferably either Fe, Co, Ni, Pd or Pt. Most preferably, M is Ni. $R^a$ and $R^b$ may be the same or different, and are independently selected from hydrogen, electron-withdrawing groups including those that are or contain heterocyclic, cyano, carboxylate, carboxylic ester, keto, nitro, and sulfonyl groups, and hydrocarbyl groups, including alkyl, cyclo alkyl, alkenyl and aryl groups, unsubstituted or fully or partly substituted. Preferably, $R^a$ and $R^b$ are substituted or unsubstituted hydrocarbyl groups. Most preferably, $R^a$ and $R^b$ are $CF_3$, $CH_3$ or phenyl groups.

As is known in the art, another type of dithiolene compound that may also be used contains benzene dithiolato ligands, represented by the structure in the formula (II) above. In the formula (II), M also is a late transition metal with the same characteristics as described for formula (I). $R^1$, $R^2$, $R^3$, and $R^4$ are independently selected and may be the same or different, and $R^1$ to $R^4$ are hydrogen, electron-withdrawing groups as described above, and unsubstituted or fully or partly substituted hydrocarbyl groups including alkyl, cycloalkyl, alkenyl, and aryl groups, preferably with substituents at the carbon atoms of the hydrocarbyl group that are electron-withdrawing groups. Preferably, the group is a halo group.

Those skilled in the art would recognize more complex forms in the dithiolene class that also may be used, as disclosed in Mueller-Westerhoff, U. T., "Dithiolene and Related Species", Comprehensive Coordination Chemistry, Vol. 2, 595–631 (1987), and McCleverty, J. A., "Metal 1,2-Dithiolene and Related Complexes", Prog. Inorg. Chem., Vol. 10, 49–221 (1968), both incorporated by reference herein.

Thus, the compound can be any late transition metal bis(1,2-enedithiolate). The compound is preferably a substituted 1,2-enedithiolate where the substituent is an aryl or alkyl group, more preferably the alkyl group is a halo-alkyl group, and most preferably the compound is the bis (dithiobenzil) metal compound or the bis[1,2-bis (trifluoromethyl)ethylene-1,2-dithiolato] metal compound.

In one embodiment, the activating cocatalyst is selected from the group consisting of alkylaluminoxanes, aluminum alkyls, aluminum halides, alkyl aluminum halides, Lewis acids, alkylating agents, and mixtures thereof. In a more preferred embodiment, the activating cocatalyst is methylaluminoxane. The preferred ratio of metal compound to activating cocatalyst is from $1:10^{-2}$ to $1:10^6$.

Lewis acids other than any of the foregoing list and the mixtures of the foregoing can also be used in conjunction with alkylating agents, such as methyl magnesium chloride and methyl lithium. Examples of such Lewis acids are those compounds corresponding to the formula: $R''''_3B$, where $R''''$ independently each occurrence is selected from hydrogen, silyl, hydrocarbyl, halohydrocarbyl, alkoxide, aryloxide, amide or combination thereof, said $R''''$ having up to 30 non-hydrogen atoms.

It is to be appreciated by those skilled in the art, that the above formula for the preferred Lewis acids represents an empirical formula, and that many Lewis acids exist as dimers or higher oligomers in solution or in the solid state. Other Lewis acids which are useful in the catalyst compositions of this invention will be apparent to those skilled in the art.

Other examples of suitable cocatalysts are discussed in U.S. Pat. Nos. 6,037,297 and 5,198,401, and PCT patent documents PCT/US97/10418 and PCT/US96/09764, all incorporated by reference herein.

The composition described above may also be supported. The support material is preferably a porous material which includes, but is not limited to, inorganic oxides, talc, and inorganic chlorides. The support material may also be resinous materials such as polystyrene polyolefin or polymeric compounds. The support material may also be any other organic material that has an average particle size greater than approximately 10 micron. These catalysts are generally physisorbed on the support. The catalysts can also be supported on mesoporous materials. In a more preferred embodiment, the composition is supported by silica.

The metal dithiolene compound of the invention is used in conjunction with the cocatalyst to oligomerize olefinic monomers. Thus, the invention also provides a method for producing linear α-olefins by contacting olefinic monomers with the composition described above under certain temperature and pressure conditions conducive to forming oligomers, while minimizing, or totally eliminating, any polymer co-product. Olefinic monomers used for producing the linear α-olefins include, but are not limited to, ethylene, propylene, butenes, and mixtures thereof. A preferred olefinic monomer is ethylene. In one embodiment, the invention produces linear α-olefins having approximately four to twenty carbon atoms. In a more preferred embodiment, the invention produces α-olefins having four to twelve carbon atoms.

The novel method advantageously oligomerizes olefinic monomers derived from crude feed streams that contain contaminants. Such contaminants include $H_2$, CO, paraffins, $C_2H_2$, $H_2O$, $CO_2$ and alkynes. However, the most harmful, and least addressed in the art, contaminants are sulfur-containing compounds. The instant method successfully oligomerizes olefinic monomers into higher olefins even with crude feeds contaminated with sulfur-containing compounds, such as $H_2S$, mercaptans, sulfides, thiophenes and derivatives thereof.

Generally, oligomerization may be accomplished utilizing similar temperatures and pressures used in the art. More specifically, temperature ranges from about −100 to 250° C. and pressures from about 5 to 30,000 psig are acceptable. The most preferred temperature range is from about 0° C. to 100° C., while the most preferred pressure range is from about 15 to 2,000 psig.

Furthermore, oligomerization may take place in a solvent, neat (e.g., no solvent and liquid condensed olefin), or in a gas phase (e.g., olefin in gas phase and catalyst in the solid phase). When oligomerization is conducted in a solvent phase, suitable solvents include, but are not limited to, ethane, propane, butane, pentane, hexane, toluene, methylene chloride, carbon dioxide and mixtures thereof.

As for oligomerization in a gas phase, ExxonMobil Chemical Corporation's gas phase catalyst technology, as described in U.S. Pat. No. 5,554,704, which is herein incorporated by reference, teaches a process for producing a supported catalyst. The supported catalyst can then be used in a solvent-free system wherein the gas phase α-olefin is passed through a fixed bed of catalyst. The condensed α-olefin product is then separated from the system.

The invention is further described in the following non-limiting examples.

EXAMPLES

Example 1

Preparation of Bis(dithiobenzil) Nickel

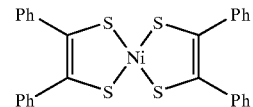

The bis(dithiobenzil) nickel compound was synthesized following the literature method of Schrauzer and Mayweg (J. Am. Chem. Soc., 1965, 87, 1483–89). Benzoin (10 g) was refluxed with 15 g of $P_4S_{10}$ in 70 mL of dioxane for 2 hr. During this time, the thiophosphoric esters of dithiobenzoin are formed and hydrogen sulfide is evolved. To the cooled and filtered reaction solution 5 g of $NiCl_2.6H_2O$ in 20 mL of water was added and the reaction mixture was heated on a steam bath for 2 hrs. Black crystals of the compound are formed and collected by filtration. The yield was 4.5 g (35% based on benzoin), m.p. 292° C. dec. UV-vis (chloroform): 866, 602, 417, 377, 316, 270 nm.

Example 2

Preparation of Bis [1,2-bis(trifluoromethyl) ethylene-1,2-dithiolato]Nickel

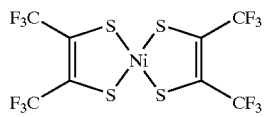

Bis(trifluoromethyl)-1,2-dithiete, $(CF_3)_2C_2S_2$, was prepared by reacting hexafluoro-2-butyne with sulfur vapor according to Krespan (J. Am. Chem. Soc., 1960, 82, 1515–16 and J. Am. Chem. Soc., 1961, 83, 3434–37). A mixture of bis(trifluoromethyl)-1,2-dithiete and its oligomers (0.45 g, 2 mmol in $(CF_3)_2C_2S_2$) was mixed with nickel powder (sub-micron size, 0.07 g, 1.1 mmol) in 20 mL of anhydrous toluene. The mixture was refluxed under argon for two days. The deep-blue solution was filtered through a fine frit to remove unreacted nickel. The solvent was removed under vacuum and a black solid was obtained. The resulting yield was 0.4 g (80%). $^{19}F$ NMR ($CDCl_3$, $C_6F_6$):s, δ–57.2. UV-vis (pentane): 715, 553, 410, 295, 230 nm.

Example 3

Ethylene Oligomerization Using $Ni(S_2C_2Ph_2)_2$

In an Ar glovebox, a toluene slurry was prepared in a 50 mL Parr glass liner by suspending compound $Ni(S_2C_2Ph_2)_2$ (21335-29-2, FW 542) (8.7 mg, $1.6 \times 10^{-2}$ mmoles) (product of Example 1) in 8.00 g toluene followed by activation with 2.01 mL of 30% MAO (Al/Ni=650) to obtain a solution. In the glovebox, the glass liner was placed into the Parr reactor. The reactor was transfer to a hood and then pressurized with 500 psig of ethylene. The solution was stirred (stirring rate 500 RPM) at 25° C. for 30 minutes. During the reaction, pressure dropped to nearly zero psig. The reaction mixture was cooled and unreacted ethylene was vented to obtain 2.4 g of product. The product was analyzed by gas chromatography-mass spectrometry. GC analysis of the product indicated peaks due to butenes (80%) and hexenes (20%). Small peaks corresponding to higher olefins were observed. Catalyst productivity was about 10680 moles ethylene reacted/moles of Ni catalyst per hour.

Example 4

Ethylene Oligomerization Using $Ni[S_2C_2(CF_3)_2]_2$

In an Ar glovebox, a toluene slurry was prepared in a 50 mL Parr glass liner by suspending compound $Ni[S_2C_2(CF_3)_2]_2$ (21335-19-1, FW 511) (9.1 mg, $1.78 \times 10^{-2}$ mmoles) (product of Example 2) in 8.07 g toluene followed by activation with 2.02 mL of 30% MAO (Al/Ni=590) to obtain a solution. In the glovebox, the glass liner was placed into the Parr reactor. The reactor was transfer to a hood and then pressurized with 500 psig of ethylene. The solution was stirred (stirring rate 500 RPM) at 25° C. for 30 minutes. During the reaction, pressure dropped to almost zero psig. The reaction mixture was cooled and unreacted ethylene was vented to obtain 2.3 g of product. The product was analyzed by gas chromatography-mass spectrometry. GC analysis of the product indicated peaks due to butenes (84%) and hexenes (16%). Small peaks corresponding to higher olefins were observed. Catalyst productivity was about 9225 moles ethylene reacted/moles of Ni catalyst per hour.

Example 5

Gas Phase Ethylene Oligomerization Using $Ni(S_2C_2Ph_2)_2$

In an Ar glovebox, a toluene slurry was prepared in a 50 mL Parr glass liner by suspending compound $Ni(S_2C_2Ph_2)_2$ (21335-29-2, FW 542) (8.9 mg, 1.64 mmoles) in 8.04 g toluene followed by activation with 2.0 g of 30% MAO (Al/Ni=630) to obtain a dark suspension. The solvent was removed under high vacuum and the residue or powder was loaded into 50 mL Parr reactor under nitrogen. The Parr reactor was pressurized with 350 psig of ethylene at 25° C. Within 3 hours, the ethylene pressure dropped from 350 psig to 80 psig. The reaction mixture was cooled and unreacted ethylene was vented to obtain 1.4 g of product. The product was analyzed by gas chromatography-mass spectrometry. GC analysis of the products indicated major peaks due to butenes and hexenes along with peaks attributed to octenes, decenes, dodecenes, and tetradecenes.

Example 6

Multi-Cycle Batch Ethylene Oligomerization Using $Ni(S_2C_2Ph_2)_2$

In an Ar glovebox, the $Ni(S_2C_2Ph_2)_2$ compound (21335-29-2, FW 542, 9.2 mg, 1.7 mmole) was suspended in 8.05 g of toluene followed by activation with 2.03 g of 30% MAO to obtain a dark suspension in a 50 mL Parr glass liner. The glass liner was placed into the Parr reactor and transferred to a hood then pressurized with 500 psig of ethylene. The solution was stirred (stirring rate 500 RPM) at 25° C. for 7 minutes. During the reaction, pressure dropped to 200 psig. The Parr reactor was repressurized with ethylene to 500 psig and the solution was stirred at 25° C. for 11 minutes. During this period, pressure dropped again to 200 psig. The repressurization and ethylene reaction were continued for 5 additional times. The catalyst was still active. Finally, the reaction mixture was cooled and unreacted ethylene was vented to obtain 9.1 g of product. The product was analyzed by gas chromatography-mass spectrometry. GC analysis of the product indicated peaks due to butenes and hexenes.

Example 7

Ethylene Oligomerization Using Supported $Ni(S_2C_2Ph_2)_2$

In a round bottom flask, the $Ni(S_2C_2Ph_2)_2$ compound (21335-29-2, FW 542, 19 mg) was dissolved into methylene chloride (16 mL) and stirred for 15 minutes. To the purplish solution 4.01 g MAO (30-wt % in toluene) was slowly added to give a greenish colored solution. After 30 minutes, silica (Grace-Davidson Grade 62 dehydrated) (0.514 g) was added and stirring was continued for 18 hrs. The flask was heated to 50° C. under vacuum (0.05 mm Hg) for 6 hours to give a dark solid.

The supported catalyst (2 g) was placed into a fritted vessel. The fritted vessel was placed into a 50 mL Parr glass liner, thus suspending the supported catalyst. The Parr reactor was sealed then pressurized to 550 psig with ethylene. The reaction was run for 6 hours at room temperature, during which period the pressure dropped from 550 psi to 280 psi. The reaction mixture was cooled and unreacted ethylene was vented to obtain 0.3 g of product. The product was analyzed by gas chromatography-mass spectrometry. GC analysis of the product indicated peaks due to butenes and hexenes.

Example 8

Ethylene Oligomerization Using Ni(S$_2$C$_2$Ph$_2$)$_2$ in the Presence of n-Propyl Mercaptan The Ni(S$_2$C$_2$Ph$_2$)$_2$ compound (10 mg) was mixed with 3 mL of a toluene solution of MAO (10%) in a 25-mL flask under N$_2$. The solid slowly dissolves after stirring. The flask was put to a vacuum-line and the overhead gas was evacuated. Ethylene was passed into the flask for 5 minutes and the flask was sealed. The mixture was stirred at room temperature for 15 minutes and then analyzed by GC/MS. Butenes, hexenes, and small amounts of higher olefins (up to C14) are formed.

To test the effect of possible contaminants on the catalyst activity, a modified procedure was adopted. Instead of passing ethylene directly to the flask containing the catalyst, the olefin stream was first passed through a 50-mL flask filled with vapor of n-propyl mercaptan (100 μL). Other conditions were kept the same. The catalyst is still active and butenes, hexenes, and small amounts of higher olefins (up to C14) are formed as detected by GC/MS.

Example 9

Ethylene Oligomerization Using Ni(S$_2$C$_2$Ph$_2$)$_2$ in the Presence of Thiophene The same procedure as that in Example 8 is used except that ethylene was first passed through a flask containing 100 μL of thiophene before reaching the catalyst. The catalyst is still active and butenes, hexenes, and small amounts of higher olefins (up to C14) are formed as detected by GC/MS.

The invention having been thus described, it will be obvious that the same may be varied in many ways without departing from the spirit and scope of the invention as defined by the following claims.

What is claimed is:

1. A method for producing oligomers having less than 40 carbon atoms using at least one olefinic monomer selected from the group consisting of ethylene, propylene, butenes, hexenes, octenes and mixtures thereof, the method comprising the step of contacting a feed comprising the olefinic monomer under oligomerizution conditions with a catalyst composition comprising the reaction product of:
   (a) a compound having a formula selected from the group consisting of M[S$_2$C$_2$(R$^a$R$^b$)]$_2$ and M[S$_2$C$_6$(R$^1$R$^2$R$^3$R$^4$)]$_2$, wherein M is a late transition metal, R$^a$, R$^b$, R$^1$, R$^2$, R$^3$ and R$^4$ are independently selected and may be the same or different and are selected from hydrogen, electron-withdrawing groups and unsubstituted and substituted hydrocarbyl groups; and
   (b) an alkylaluminoxane activating cocatalyst, whereby an oligomer is formed.

2. The method of claim 1 wherein M is selected from one of Fe, Co, Ni, Pd, and Pt.

3. The method of claim 1 wherein the compound is selected from the group consisting of bis(dithiobenzil) nickel and bis[1,2-bis(trifluoromethyl)ethylene-1,2-dithiolato] nickel.

4. The method of claim 1 wherein the cocatalyst is methylaluminoxane.

5. The method of claim 1 wherein the contacting is at a temperature in the range of from about 0° C. to 100° C. and at pressures of from about 15 to 2000 psig.

6. The method of claim 1 wherein the contacting is conducted in a solvent.

7. The method of claim 1 wherein the contacting is conducted in a gas phase.

8. The method of claim 1 wherein said olefinic monomer is ethylene.

9. The method of claim 1 wherein the catalyst composition comprises a supported catalyst composition.

10. The method of claim 9 wherein the supported catalyst composition comprises a silica supported catalyst composition.

11. The method of claim 1 wherein the feed contains contaminants.

12. The method of claim 11 wherein the contaminants comprise sulfur-containing compounds.

13. The method of claim 12 wherein the sulfur-containing compounds comprise H$_2$S, mercaptans, sulfides and thiophenes.

14. A method for producing oligomers having less than 40 carbon atoms using at least one olefinic monomer selected from the group consisting of ethylene, propylene, butenes, hexenes, octenes and mixtures thereof, wherein the olefinic monomer is from a feed stream having sulfur-containing compounds, the method comprising the step of contacting the feed stream under oligomerization conditions with a catalyst composition comprising the reaction product of:
   (a) a compound having a formula selected from the group consisting of M[S$_2$C$_2$(R$^a$R$^b$)]$_2$ and M[S$_2$C$_6$(R$^1$R$^2$R$^3$R$^4$)]$_2$, wherein M is a late transition metal, R$^a$, R$^b$, R$^1$, R$^2$, R$^3$ and R$^4$ are independently selected and may be the same or different and are selected from hydrogen, electron-withdrawing groups and unsubstituted and substituted hydrocarbyl groups; and
   (b) an alkylaluminoxane activating cocatalyst, whereby an oligomer is formed.

* * * * *